United States Patent [19]

Chasar

[11] Patent Number: 4,495,320
[45] Date of Patent: Jan. 22, 1985

[54] 3,6-DI-T-BUTYL-2-NAPHTHYL CATECHOL PHOSPHITE AND COMPOSITIONS THEREOF

[75] Inventor: Dwight W. Chasar, Northfield, Ohio

[73] Assignee: The B. F. Goodrich Company, Akron, Ohio

[21] Appl. No.: 498,622

[22] Filed: May 27, 1983

[51] Int. Cl.$^3$ .................. C08K 5/34; C08K 5/52
[52] U.S. Cl. .................. 524/101; 260/937; 524/117
[58] Field of Search .................. 260/937; 524/101, 117

[56] References Cited

U.S. PATENT DOCUMENTS

| | | | |
|---|---|---|---|
| 2,058,343 | 10/1936 | Moran et al. | 260/967 |
| 3,796,684 | 3/1974 | Dever et al. | 524/117 |
| 4,025,486 | 5/1977 | Gilles | 524/101 |
| 4,184,999 | 1/1980 | Olander | 524/117 |
| 4,187,212 | 2/1980 | Zinke et al. | 524/101 |
| 4,341,880 | 7/1982 | Toyoda et al. | 524/101 |
| 4,351,759 | 9/1982 | Spivack | 524/101 |

OTHER PUBLICATIONS

Levin et al., Chem. Abs., vol. 61, 1964, 9634e.

*Primary Examiner*—John Kight, III
*Assistant Examiner*—R. A. White
*Attorney, Agent, or Firm*—J. Hughes Powell, Jr.; Alan A. Csontos; Carl W. Battle

[57] ABSTRACT

3,6-di-t-butyl-2-naphthyl catechol phosphite is readily prepared by the reaction of catechol phosphorodichloridite and 3,6-di-t-butylnathphol in the presence of a trialkyl amine in a solvent. The 3,6-di-t-butyl-2-naphthyl catechol phosphite is an excellent stabilizer for polymers, including polypropylene, and forms synergistic combinations with hydroxyphenylalkyleneyl isocyanurates that provide excellent resistance to polymer breakdown during processing.

10 Claims, No Drawings

3,6-DI-T-BUTYL-2-NAPHTHYL CATECHOL PHOSPHITE AND COMPOSITIONS THEREOF

The use of certain catechol phosphites as antioxidants in polypropylene is disclosed in Chemical Abstracts 61:9634e (1964). This article reports the effect of various phosphites on the induction period in the oxidation of isotactic polypropylene at 200° and 200 mm 0 pressure. The following order of increasing effectiveness as antioxidant was found: trinonyl phenyl phosphite, pyrocatechol phosphite, phenyl pyrocatechol phosphite, 4-tert-butyl phenyl pyrocatechol phosphite, -naphthyl pyrocatechol phosphite, 2,6-di-tert-butyl-4-methylphenyl pyrocatechol phosphite, and 2,4,6-tri-tert-butylphenyl pyrocatechol phosphite. Two component antioxidants consisting of one of the above phosphites plus one of the following compounds were evaluated: 2,2'-thiobis(6-tert-butyl-4-methylphenol), 4,4'-thiobis(2-tert-butyl-5-methylphenol), mercaptobenzimidazole, and 2,2'-dithiobis(6-tert-butyl-4-methylphenol). Synergism was noted for mixtures of phosphites with the monosulfides, but antagonism was found with mixtures of phosphites with disulfides or mercaptans.

U.S. Pat. No. 4,184,999 discloses compositions of polyphenylene ether resins and alkyl aromatic resins modified with rubber and a hindered phenol as a stabilizer. Hindered phenols disclosed included 2,6-di-tert-butyl-4-methylphenol, 4,4-methylene bis(2,6-di-tert-butylphenol), 2,6-di-tert-butyl-4-n-butyl-phenol, 2,4,6-tris(3'-5-di-tert-butyl-4-hydroxybenzyl)-1,3,5-triazine, tetrakis[methylene 3-(3',5'-di-tert-butyl-4'-hydroxyphenyl)propionate]methane, and stearyl-3-(3'-5'-di-tert-butyl-4'-hydroxyphenyl)propionate. Admixtures of the hindered phenols nd alkylamines or phosphites are suggested, including dimethyl octadecylamine and catechol-2,6-di-tert-butyl-4-methyl-phenol-phosphite.

SUMMARY OF THE INVENTION 3,6-di-t-butyl-2-naphthyl catechol phosphite has been found, quite unexpectedly, to be a good antioxidant for polyolefins, as shown by resistance to oven ageing, when compared to 3,6,8-tri-t-butyl-2-naphthyl catechol phosphite. Synergistic combinations obtained from the combination of 3,6-di-t-butyl-2-naphthyl catechol phosphite and a hydroxyphenylalkyleneyl isocyanurate provide even better protection to polyolefins as shown by oven ageing results. This combination also provides outstanding process stability in polyolefins such as polypropylene and provide excellent protection against changes in the melt flow index of polyolefins during processing.

DETAILED DESCRIPTION

The prior art might suggest to the man skilled in the art that highly alkylated naphthyl moities in 2-naphthyl catechol phosphite type compounds would be excellent antioxidants. However, this has not been found to be the case. It has been found, quite unexpectedly, that 3,6,8-tri-t-butyl-2-naphthyl catechol phosphite is far less effective as an antioxidant than the disubstituted 3,6-di-t-butyl-2-naphthyl catechol phosphite. This difference is demonstrated even more vividly when the 3,6-di-t-butyl-2-naphthyl catechol phosphite of this invention is combined with a hydroxyphenylalkyleneyl isocyanurate. The 3,6-di-t-butyl-2-naphthyl catechol phosphite is readily prepared from equimolar ratios of catechol phosphorochloridite, and 3,6-di-t-butyl-2-naphthol in the presence of an amine catalyst in an organic solvent. A typical preparation is described in Example I.

EXAMPLE I

3,6-di-t-butyl-2-naphthyl Catechol Phosphite 6.0 weight parts of 3,6-di-t-butyl-2-naphthol was dissolved in 86.7 weight parts of dry toluene and the solution cooled to about 6° C. Under nitrogen, 4.08 weight parts of catechol phosphorochloridite was added to the solution. Then 2.37 weight parts of triethyl amine was added slowly to the cooled solution with stirring. This solution was stirred for about 16 hours at room temperature. The reaction mixture was filtered, washed twice with water, dried with $MgSO_4$, and rotoevaporated to remove all traces of toluene. A gray oil was obtained. A product yield of 57 weight percent was obtained. The expected structure was confirmed by infra red and nuclear magnetic resonance spectra, and the molecular weight by the field desorption/mass spectrum.

EXAMPLE II

3,6,8-tri-t-butyl-2-naphthyl Catechol Phosphite 6.0 weight parts of 3,6,8-tri-t-butylnaphthol was dissolved in 86.7 weight parts of dry toluene and the solution cooled to about 6° C. Under nitrogen, 3.36 weight parts of catechol phosphorochloridite was added to the solution. 1.95 weight parts of triethyl amine was added slowly to the cooled stirred solution. The reaction was allowed to continue for 16 hours at room temperature. 69 weight percent product was obtained. The reaction mixture was filtered, washed twice with water, dried over $MgSO_4$ and rotoevaporated to remove all traces of toluene. An oil was obtained that solidified. This solid was stirred in acetone and a white powder was obtained that had a melting point of 140°–142° C. The expected structure was confirmed by infra red and nuclear magnetic resonance spectra. The molecular weight was confirmed by the field desorption/mass spectrum.

Test samples of 3,6-di-t-butyl-2-naphthyl catechol phosphite and 3,6,8-tri-t-butyl-2-naphthyl catechol phosphite in polypropylene were prepared by mixing the stabilizer compounds with polypropylene in a Brabender Plasticorder fitted with a Cam-Head (mixing chamber). The polypropylene was first masticated for 1½ minutes at 190° C. Then the stabilizer was added, followed by 3 minutes additional mixing. The mass was removed and pressed into 20 mil thick sheets. From these sheets, 1"×1" plaques were cut for oven ageing.

Thermal/oxidative stability (oven ageing) testing consisted of ageing the samples in triplicate in an air-circulating oven at 125° C. The time to catastrophic crumbling (failure) of the plaque was measured and reported as days to failure. Each sample contained 0.1 weight part of alkyl substituted-2-naphthyl catechol phosphite per 100 weight parts of polypropylene. The following results were obtained:

3,6,-di-t-butyl-2-naphthyl catechol phosphite: 15⅝ days
3,6,8-tri-t-butyl-2-naphthyl catechol phosphite: 7 days The hydroxyphenylalkyleneyl isocyanurate compounds used in combination with the 3,6-di-t-butyl-2-naphthyl catechol phosphites have the formula

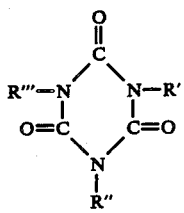

wherein R' is a hydroxyphenylalkyleneyl radical of the formula

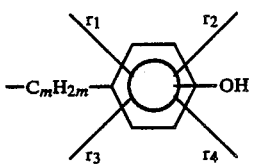

where m is 1 to 4, $r_1$ is an alkyl radical having 1 to 18 carbon atoms and is positioned immediately adjacent to the hydroxy group on the ring; $r_2$, $r_3$ and $r_4$ are hydrogen or an alkyl radical containing 1 to 18 carbon atoms; and R'' and R''' are hydrogen, alkyl radical containing 1 to 18 carbon atoms, or are the same as R'. A more preferred compound is when R'' and R''' are equal to R', i.e., all the R groups are hydroxyphenylalkyleneyl radicals, and $r_1$ is a t-alkyl radical containing from 4 to about 12 carbon atoms, $r_2$ is a t-alkyl radical containing from 4 to about 12 carbon atoms, $r_3$ and $r_4$ are hydrogen, and m=1.

Even more preferred are the symmetrical tris(3,5-di-tert-alkyl-4-hydroxybenzyl)isocyanurates of the formula

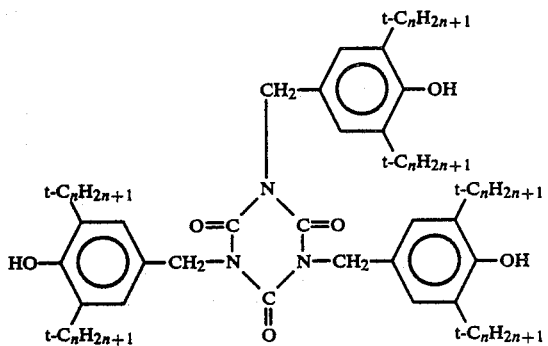

wherein n is 4 to 8.

Examples of the 4-hydroxybenzyl isocyanurate compounds are: tris(3-t-butyl-4-hydroxybenzyl)isocyanurate, tris(3-cetyl-4-hydroxybenzyl)isocyanurate, tris(3,5-dimethyl-4-hydroxybenzyl)isocyanurate, tris(3-methyl-5-isopropyl-4-hydroxybenzyl)isocyanurate, tris(3,5-di-t-butyl-4-hydroxybenzyl)isocyanurate, tris(3-t-butyl-5-t-amyl-4-hydroxybenzyl)isocyanurate, tris[3,5-di-(1-methyl-1-ethylpropyl)-4-hydroxybenzyl]isocyanurate, tris[3,5-di-(1,1,2,2-tetramethylpropyl)-4-hydroxybenzyl]isocyanurate, bis-(3,5-dimethyl-4-hydroxybenzyl)isocyanurate, (3-methyl-4-hydroxybenzyl)isocyanurate, (3-t-butyl-4-hydroxybenzyl)isocyanurate and the like. Reference is made to U.S. Pat. No. 3,531,483 which discloses isocyanurate compounds encompassed by this invention. This disclosure of this patent is incorporated herein by reference.

The amount of 3,6-di-t-butyl-2-naphthyl catechol phosphite used may vary from about 0.01 to 10 weight parts per 100 weight parts of material to be stabilized. More usually about 0.1 to 5.0 parts are used for mixtures with the hydroxyphenylalkyleneyl isocyanurate. The hydroxyphenylalkyleneyl isocyanurate compound is used at a level from about 0.01 part to about 1 to 5 parts by weight, and more preferably at from about 0.05 part to about 3 parts by weight per 100 parts by weight of the organic material. The 3,6-di-t-butyl-2-naphthyl catechol phosphite is employed at similar levels, i.e., from about 0.01 part to 5 parts and preferably at about 0.05 part to about 3 parts by weight per 100 parts by weight of organic material. Thus the combined weight of the compounds is normally from about 0.02 part to about 10 parts and more preferably from about 0.05 to 5 parts by weight per 100 parts by weight of organic material. The hydroxyphenylalkyleneyl isocyanurate can be used in from about 10:1 to 1:10 weight ratio of isocyanurate compound to the 3,6-di-t-butyl-2-naphthyl catechol phosphites. Excellent results are obtained at about a 3:1 to 1:3 weight ratio. A 1:1 weight ratio of the compounds provides effective stabilization of organic materials.

Test samples of polypropylene with 0.05 weight part each of tris(3,5-di-t-butyl-4-hydroxybenzyl)isocyanurate, and 2-naphthyl catechol phosphites were prepared and tested in the air oven until failure. The results obtained were as follows:

3,6-di-t-butyl-2-naphthyl catechol phosphite: 114 days
3,6,8-tri-t-butyl-2-naphthyl catechol phosphite: 26⅓ days Control samples of polypropylene containing 0.05 and 0.1 phr of tris(3,5-di-t-butyl-4-hydroxybenzyl) isocyanurate only, failed after 13⅔ and 25⅓ days, respectively. This clearly demonstrates the unexpected synergistic enhancement of antioxidant activity obtained when the 3,6-di-t-butyl-2-naphthyl catchol phosphite of this invention is combined with hydroxyphenylalkyleneyl isocyanurates.

The sample of polypropylene containing 0.1 weight part of tris(3,5-di-t-butyl-4-hydroxybenzyl)isocyanurate only failed after about 25⅓ days. This is to be contrasted to the synergistic combination about wherein only 0.05 weight parts of the tris (3,5-di-t-butyl-4-hydroxybenzyl) isocyanurate in combination with 0.05 weight part of the 3,6-di-t-butyl-2-naphthyl catechol phosphite did not fail after more than 100 days!

Based on the teaching of the prior art, one might expect to obtain effective combinations of a hydroxyphenylalkyleneyl isocyanurate and phenyl catechol phosphites as the alkyl substitution on the phenyl nucleus was increased, but this is not what is obtained as can be seen from the data below, obtained by following the procedure set forth above for preparing polypropylene samples containing 0.05 phr each of the isocyanurate and the phenyl catechol phosphite:

2,4,6-tri-t-butylphenyl catechol phosphite: 21 days.

The 3,6-di-t-butyl-2-naphthyl catechol phosphite was evaluated for its effect on the melt flow properties of a polymeric material, polypropylene, during multiple extrusions at 270° C. The additives and polymer were dry blended at room temperature. A concentrate was first prepared by mixing part of the polymer and additives for three minutes in the Brabender mixer equipped with sigmoid blades. The concentrate was then mixed with the remainder of the polymer in the Henschel mixer. The incorporation of the additives was completed by extruding at 215° C. After incorporation and pelletizing, a sample of each experiment was taken for testing. The remaining polymer was again extruded, this time at 270° C., water cooled, pelletized and sampled. This procedure was repeated for a total of five extruder passes at 270° C.

The melt flow was determined by following the ASTM D-1238, Condition L procedure. Three specimens for each sample were collected for weighing and determining the melt flow index (MFI). If one of the specimens showed an apparent difference in MFI from the other two, a statistical formula was applied and the questionable result discarded if the confidence factor was less than 95%. The average values of the MFI are noted. Plots of melt flow versus extruder passes were made. Linear regression was used to obtain the best fit for the line graphs of the data and the slopes were calculated for these line graphs.

A control of polypropylene only had a melt index after 1 pass of 8.54, after 3 passes of 12.14, and after 5 passes of 18.00. When the sample contained 0.05 phr of 3,6-di-t-butyl-2-naphthyl catechol phosphite, the melt index after 1 pass was only 3.19, after 3 passes was 5.61, and after 5 passes was 8.04. The slopes were 2.37 and 1.21 respectively. These data clearly illustrate the substantial effect of 3,6-di-t-butyl-2-naphthyl catechol phosphite in preventing undesirable melt flow change during processing of polypropylene.

The combination of isocyanurate compound and the 3,6-di-t-butyl-2-naphthyl catechol phosphite provide exceptional heat stability to polyolefin polymers. The combination is especially useful for the stabilization of α-monoolefin homopolymers and copolymers, wherein the α-monoolefin contains 2 to about 8 carbon atoms. High and low-density polyethylene, isotactic and atactic polypropylene, poly-isobutylene, and poly(4-methyl-1-pentene) have excellent resistance to heat and oxygen when stabilized with the combinations of the present invention. Ethylene-propylene copolymers and ethylene-propylene terpolymers, generally containing less than about 10 percent by weight of one or more monomers containing multiple unsaturation provided, for example, by 1,4-hexadiene, dimethyl-1,4,9-decatriene, dicyclopentadiene, vinyl norborene, ethylidene norborene, and the like, also provide excellent ageing properties using the composition of this invention.

Other organic materials which can be stabilized in accordance with the present invention include both natural and synthetic polymers. For example, the stabilizers are useful for the stabilization of cellulosic materials; natural rubber, halogenated rubber, conjugated diene polymers, as, for instance, polybutadiene, copolymers of butadiene with styrene, acrylonitrile, acrylic acid, alkyl acrylates or methacrylates, methyl vinyl ketone, vinyl pyridine, etc.; polyisoprene, polychloroprene, and the like; vinyl polymers such as poly(vinyl chloride), poly(vinylidene chloride), copolymers of vinyl chloride with vinylidene chloride, polyvinyl acetate, copolymers or vinyl halide with butadiene, styrene, vinyl esters, α,β-unsaturated ketones and aldehydes, and the like; homopolymers and copolymers of acrylic monomers such as acrylic acid, methacrylic acid, methyl acrylate, methyl methacrylate, ethyl acrylate, 3-ethylhexyl acrylate, acrylamide, methacrylamide, N-methylol-acrylamide, haloacrylates, acrylonitrile, methacrylonitrile, haloacrylates, and the like; epihalohydrin polymers; polyether- or polyol-derived polyurethanes; acetal homopolymers and copolymers; polycarbonates; polyesters such as those derived from maleic, fumaric, itaconic, or terephthalic anhydrides; for example, polyethylene terephthalate; polyamides such as those derived from the reaction of hexamethylenediamine with adipic or sebacic acid; epoxy resins such as those obtained from the condensation of epichlorohydrin with bisphenols; ring opened olefin polymers and the like. Polymer blends, that is, physical admixture of two or more polymers may also be stabilized in accordance with the present invention.

In addition to polymeric materials, the present compounds may stabilize a wide variety of other organic materials. Such compounds include; waxes, synthetic and petroleum-derived lubricating oils and greases; animal oils such as, for example, fat, tallow, lard, cod-liver oil, sperm oil; vegetable oils such as castor, linseed, peanut, palm, cotton seed, and the like; fuel oil; diesel oil, gasoline and the like.

The compounds are readily incorporated into materials to be patented by dissolving or dispersing them with the materials, in liquids, dispersions, solutions, and solid forms. If the material is a solid, especially a polymeric solid such as rubber or a plastic, the compounds can be admixed using mixers such as Banburys, extruders, two-roll mills, and the like, following conventional techniques. One way to disperse the compounds in plastic materials is to dissolve or suspend the compounds in a solvent or diluent, mix the mixture with a plastic in powder or solution form, and then evaporate the solvent.

Compositions containing the novel combination of compounds can also contain other known compounding ingredients such as fillers like carbon black, silica, metal carbonates, talc, and the like; pigments and colorants; curative ingredients like sulfur and peroxides, and vulcanization accelerators; fungicides; processing aids, reinforcing agents and standard ingredients known to the art. Other ingredients known in the art as ultra violet light, thermal and/or oxidative stabilizers can also be used in the stabilized compositions.

I claim:

1. A composition comprising materials subject to degradation and a stabilizing amount of 3,6-di-t-butyl-2-naphthyl catechol phosphite.

2. A composition of claim 1 wherein said material is a polymer.

3. A composition of claim 2 wherein said polymer is a polyolefin.

4. A composition of claim 3 wherein said polyolefin is polypropylene.

5. A composition comprising organic materials subject to degradation and stabilizing amounts of (1) 3,6-di-t-butyl-2-naphthyl catechol phosphite and (2) hydroxyphenylalkyleneyl isocyanurates of the formula

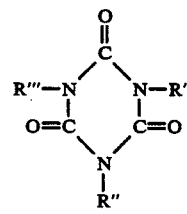

wherein R' is a hydroxyphenylalkyleneyl radical of the formula

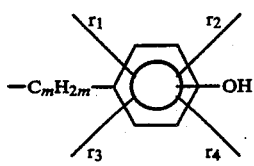

where m is 1 to 4, $r_1$ is an alkyl radical having 1 to 18 carbon atoms and is positioned immediately adjacent to the hydroxy group on the ring; $r_2$, $r_3$ and $r_4$ are hydrogen or an alkyl radical containing 1 to 18 carbon atoms; and R" and R'" are hydrogen, alkyl radical containing 1 to 18 carbon atoms, or are the same as R'.

6. A composition of claim 5 wherein said organic material is a polymer, and in (2) R" and R'" are equal to R', $r_1$ is a tertiary alkyl radical containing 4 to 12 carbon atoms, $r_3$ and $r_4$ are hydrogen, and m is 1.

7. A composition of claim 6 wherein (2) has the formula

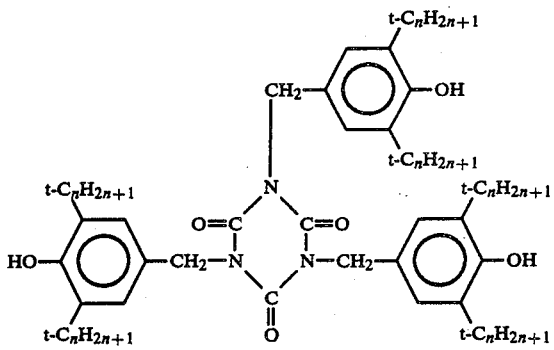

wherein n is 4 to 8.

8. A stabilizer composition of claim 7 where (2) is 1,3,5-tris(3,5-di-t-butyl-4-hydroxybenzyl) isocyanurate.

9. A composition of claim 8 wherein said polymer is a polyolefin.

10. A composition of claim 9 wherein said polyolefin is polypropylene.

* * * * *